(12) United States Patent
Kaiser et al.

(10) Patent No.: US 10,000,806 B2
(45) Date of Patent: Jun. 19, 2018

(54) TRIPLEX EVENT-SPECIFIC REACTION USED TO QUANTIFY SPECIFIC EVENTS AND POSSIBLE CONTAMINATING EVENTS

(71) Applicant: Dow AgroSciences LLC, Indianapolis, IN (US)

(72) Inventors: Tina Marie Kaiser, Carmel, IN (US); Stephen Novak, Westfield, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 452 days.

(21) Appl. No.: 14/720,511

(22) Filed: May 22, 2015

(65) Prior Publication Data

US 2015/0344949 A1    Dec. 3, 2015

Related U.S. Application Data

(60) Provisional application No. 62/003,878, filed on May 28, 2014.

(51) Int. Cl.
*C12Q 1/68*    (2018.01)

(52) U.S. Cl.
CPC .......... *C12Q 1/6876* (2013.01); *C12Q 1/686* (2013.01); *C12Q 1/6813* (2013.01); *C12Q 2600/13* (2013.01); *C12Q 2600/16* (2013.01)

(58) Field of Classification Search
USPC .............................................. 435/6.12, 91.2
See application file for complete search history.

(56) References Cited

U.S. PATENT DOCUMENTS

| | | | |
|---|---|---|---|
| 2007/0117106 A1* | 5/2007 | Remacle | C12Q 1/6895 435/6.12 |
| 2007/0148648 A1 | 6/2007 | Dugas et al. | |
| 2012/0222153 A1 | 8/2012 | Cui et al. | |
| 2012/0244533 A1 | 9/2012 | Zhou et al. | |
| 2013/0095485 A1* | 4/2013 | Channabasavaradhya | C12Q 1/6895 435/6.11 |
| 2013/0095486 A1* | 4/2013 | Channabasavaradhya | C12Q 1/6895 435/6.11 |

* cited by examiner

*Primary Examiner* — Kenneth R Horlick
(74) *Attorney, Agent, or Firm* — Michael R. Asam; Magleby Cataxinos & Greenwood

(57) ABSTRACT

Disclosed herein are methods for determining if a contaminating integration of a nucleotide sequence is present in a set of nucleic acids. Further disclosed herein are methods for determining the copy number/zygosity of a nucleic acid sequence of interest. The methods disclosed herein may be performed using quantitative PCR.

15 Claims, 7 Drawing Sheets

US 10,000,806 B2

TRIPLEX EVENT-SPECIFIC REACTION USED TO QUANTIFY SPECIFIC EVENTS AND POSSIBLE CONTAMINATING EVENTS

PRIORITY CLAIM

This application claims the benefit of the filing date of U.S. Provisional Patent Application Ser. No. 62/003,878, filed May 28, 2014, for "COMBINED METHODOLOGY USED TO DETECT THE PRESENCE OF POSSIBLE CONTAMINATING EVENTS."

BACKGROUND OF THE INVENTION

Field of the Invention

The present application relates to molecular methods for determining if a contaminating integration of a nucleotide sequence is present in a set of nucleic acids and to methods for determining the zygosity of a particular sequence.

State of the Art

Trait purity is an essential part of producing genetically modified organisms. Previously, Southern blot technology and INVADER® technology were the only methods available to distinguish if a particular nucleotide sequence had integrated at unintended locations. However, Southern blot analysis involves a large amount of labor and has sample throughput limitations. Further, INVADER® technology will only reveal if a copy of the nucleotide sequence has integrated into the genome; it will not reveal if the nucleotide sequence has also integrated at any specific location.

BRIEF SUMMARY OF THE INVENTION

Described herein are methods of determining if a contaminating integration of a nucleotide sequence is present in a set of nucleic acids. Such method comprise a first assay to determine the number of copies of the nucleotide sequence in the set of nucleic acids (a sequence specific assay) and a second assay to determine the number of copies of the nucleotide sequence which have integrated at a particular site in the set of nucleic acids (an event specific assay). Comparison of the results of the sequence specific assay and the event specific assay will reveal if there has been contaminating integration events of the nucleotide sequence at sites other than at the particular site.

Such methods may comprise performing a Polymerase Chain Reaction (PCR) with a first set of primers, wherein the primers of the first set of primers are complementary to sites internal to the nucleotide sequence of interest (sequence specific) and performing a PCR with a second set of primers, one primer of the second set being complementary to a sequence outside the nucleotide sequence of interest and one primer of the second set being complementary to a site internal to the nucleotide sequence of interest (event specific). After the PCRs are performed, a value for the amount of a first PCR product resulting from the PCR from the first set of primers is determined and a value for the amount of a second PCR product resulting from the PCR from the second set of primers determined. The values are then compared to indicate if the nucleotide sequence of interest is present at a site other than the particular integration site.

Further described herein are methods of determining the copy number of a nucleotide sequence of interest. Such methods comprise performing PCR with a third set of primers, wherein the primers of the third set of primers are complementary to sites for which the copy number is known. After the PCRs are performed, a value for the amount of a first PCR product resulting from the PCR from the first set of primers is determined and a value for the amount of a third PCR product resulting from the PCR from the third set of primers is determined. The values are then compared. As the copy number of the binding sites for the third set of primers is known, the copy number of the nucleotide sequence of interest may be derived.

The methods of determining the number of copies of a nucleotide sequence of interest integrated at sites other than a particular integration site in a set of nucleic acids may be combined with the methods of determining the copy number of a nucleotide sequence of interest.

The assays in the above methods may be performed separately or in a single reaction in a single tube or vessel.

PCR may be qPCR so that the relative number of each PCR template may be quickly and easily determined.

DETAILED DESCRIPTION OF THE INVENTION

Figure 1:
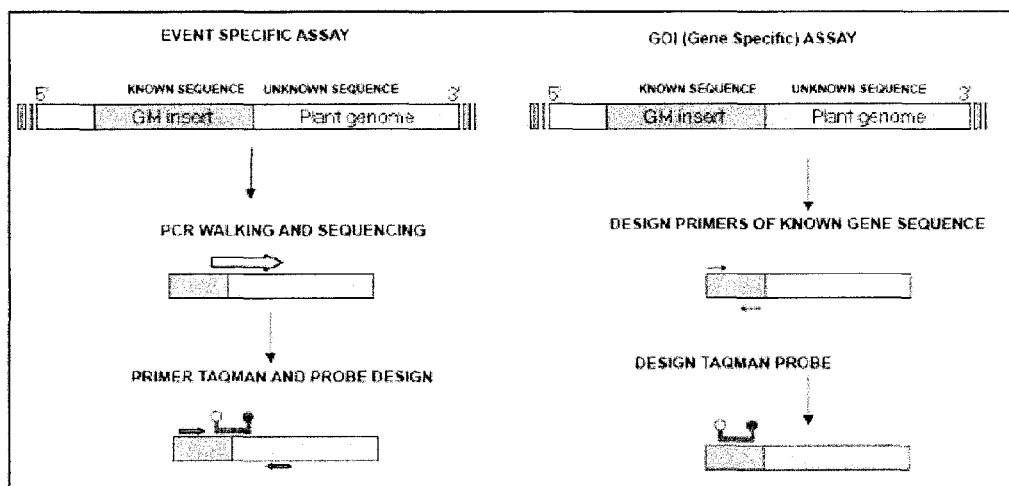
FIG. 1 is a depiction of the design of the Event Specific Assay and the Gene of Interest (GOI) specific assays.

Trait purity is an essential part of producing GM (genetically modified) plants. To effectively assay trait purity, a protocol combining an event specific assay with a gene specific zygosity/copy number assay was developed. This protocol was used in developing both a system with two separate reactions and as a single tube assay. In the two separate reactions, an event specific assay with end-point analysis was run in a high-throughput format with a second reaction consisting of a gene (or sequence) specific (GOI) assay. The single tube assay was further designed using by combining an event-specific assay plus a quantitative gene specific (GOI) assay to detect a specific transgenic event in GM crops. By comparing zygosity/copy number data between event-specific and gene-specific assays, a contaminating event of the same gene of interest can be detected.

Previously, Southern blot technology was the only method available to distinguish between different events of the same gene. However, Southern blot analysis involves increased labor and has sample throughput limitations. New technologies, such as real-time qPCR, INVADER®, Scorpion, and KASPAR type assays for event specific and/or sequence specific assays provides a simple, inexpensive and a quick procedures offering a great increase in sample throughput.

This general principal can be used for any transgenic event produced provided both event specific and gene specific assays are available. This new technique is extremely important because it can determine event purity for material already developed as well as any new events being produced through the introgression pipeline.

The utilization of qPCR technology by combining an event specific zygosity assay with a gene specific copy number assay was developed. By combining the analysis of these two assays, the adventitious presence of an event containing the same genes can be detected. If a GM plant sample is different for the copy number/zygosity status for the event specific assay as compared to the gene specific assay, a contaminating event has been detected. These results also provide the zygosity status of the contaminating event. Previously, Southern blot technology was used to detect an unknown contaminating event. Southern blot technology can be a long and laborious procedure; however, qPCR using, for example, TaqMan technology, is a simple and quick procedure.

In embodiments, disclosed are methods of the copy number and/or location of a naturally occurring nucleotide sequence or introduced nucleotides sequence in the genome of an organism. The location may be a particular integration site that has been found or selected for the introduction of the nucleotide sequence.

In other embodiments the nucleotide sequence may encode a protein or an RNA, be a gene, or comprise a regulatory site or sequence. An RNA may be a mRNA, tRNA, rRNA, pre-mRNA, piRNA, siRNA, tasiRNA, hpRNA, miRNA, or an RNA designed to take part in RNAi.

In some embodiments the nucleotide sequence may encode a protein that is associated with a particular trait. The trait may be a plant trait. Such plant traits include, but are not limited to, herbicide resistance, insect resistance, seed number, drought resistance, sugar profile, and oil profile. Examples of plants for which the disclosed methods are useful include, but are not limited to, corn, soybean, rapeseed, canola, rice, sorghum, sunflower, and cotton.

Embodiments include methods of determining if a contaminating integration of a nucleotide sequence is present outside the intended integration site in a larger sequence or set of nucleic acids. In embodiments, specific technologies such as INVADER®, Scorpion, KASPAR and PCR assays may be used for event specific assays and sequence specific assays. One type of assay may be used for the sequence specific assay and a different or the same type of assay may be used for the event specific assay. In some embodiments, PCR utilizing two sets of primers may be used. The first set of primers will each specifically bind to separate locations internal to the nucleotides sequence of interest. This set of primers is pictorially represented in the GOI assay of FIG. 1. The second set of primers will comprise at least one primer that specifically binds to a location internal to the nucleotide sequence of interest and at least one primer that specifically binds to a sequence in the larger sequence outside of the nucleotide sequence of interest. This set of primers is pictorially represented in the event specific assay of FIG. 1. In embodiments, the primer that specifically binds to a sequence in the larger sequence outside of the nucleotide sequence of interest binds to site near to the nucleotide sequence of interest. In embodiments, one primer from the first set and one primer from the second set may be the same. The two sets of primers may be used as part of a single PCR or as part of two separate PCRs.

Embodiments may further include the use of at least two probes (also referred to as reporters herein) and qPCR. A first probe will specifically bind to a site within the nucleotide sequence of interest that is between the binding sites for the primers in the first set of primers. This probe is pictorially represented in the GOI assay of FIG. 1. A second probe will bind to a location that bridges an interface between the nucleotide sequence of interest and the larger nucleotide sequence that is between the primers of the second set of primers. This probe is pictorially represented in the event specific assay of FIG. 1. The probes may comprise a nucleic acid. The probes are designed such that each time one of the primers is extended through the binding site of the probe a signal is produced. One example of such a probe is a TaqMan probe that comprises both a fluorophore and a quenching molecule. When the primer is extended via PCR through the binding site to which the probe is bound, the nucleotide sequence of the TaqMan probe is destroyed, thus separating the flurophore and the quenching molecule. Once separated, the fluorophore is no longer quenched and can be used to produce a detectable signal. TaqMan probes and quantitative PCR using such probes is well known in the art.

During the PCR(s), the first set of primers will produce PCR products in an amount and number related to the number of copies of the nucleotide sequence of interest that are present in the original sample. As such, the first probe will provide a signal that directly relates to the number of copies of the nucleotide sequence of interest that are present. The second set of primers will produce PCR products in an amount and number related to the number of copies of the nucleotide sequence to which they bind. However, the second probe will only produce a signal if the primers are extended via PCR through the site to which the second probe binds. As the second probe binds to the interface between the sequence of interest and the larger sequence at the specific integration point, only sequences where the sequence of interest was integrated in the larger sequence at the specific integration point will produce a binding site for the second probe and thus produce a signal.

In embodiments, the signal from the first probe and the signal from the second probe can be compared for signal intensity/strength. If the signal from the first probe and the signal from the second probe are of the same intensity/strength, then each copy of the nucleotide sequence of interest is integrated at the same location in the larger sequence. However, if the signal from the first probe has a higher intensity/strength than the signal from the second probe, this indicates the presence of a copy of the nucleotide sequence of interest that is not integrated at the specific integration site.

Embodiments include methods of determining the copy number of a nucleotide sequence of interest. In embodiments, PCR utilizing two sets of primers may be used. The first set of primers will each specifically bind to separate locations internal to the nucleotides sequence of interest. The second set of primers will each specifically bind to separate locations in a control sequence whose copy number is known and that is external to the nucleotide sequence of interest. The two sets of primers may be used as part of a single PCR or as part of two separate PCRs. The relative amounts of the PCR products may be determined by isolating and analyzing the PCR products or by the use of probes in a qPCR as described above. By comparing the results of the PCR from the first set of primers with the results of the second set of primers, the copy number relative to the control sequence may be determined.

In further embodiments, the methods for determining the copy number of a nucleotide sequence of interest may be combined with the methods of determining if each copy of a nucleotide sequence of interest is integrated at the same specific location in a larger sequence. In such combined methods, three sets of primers will be required: a first set of primers internal to the nucleotide sequence of interest; a second set of primers internal to a control sequence whose copy number is known; and a third set of primers comprising at least one primer that specifically binds to a location internal to the nucleotide sequence of interest and at least one primer that specifically binds to a sequence in the larger sequence outside of the nucleotide sequence of interest. The PCRs may be performed separately, combined pairwise, or combined all together in a single tube.

Demonstrated herein is the use of a new combined methodology to detect the unintended presence of GM events generated with the same gene of interests. It also demonstrates the versatility of this application using three different types of analysis (INVADER® and qPCR TaqMan in either a single or two tubes), with two different sets of nucleotide sequence of interest and Event Specific assays across two different crops. This new technology can be applied with any nucleotide sequence of interest and Event specific combinations. This technique may be applied to back-cross generations with segregating populations to detect if a variance in copy number exists as demonstrated with corn breeding samples as set forth below.

EXAMPLES

Example 1: Materials and Methods

DNA Extraction from Corn Leaf Samples:
  qPCR:
  gDNA was extracted from fresh leaf tissue samples with at least 4 disc punches following a modified laboratory protocol for the Qiagen 96-well DNeasy Kit (Cat #69181)[2] or MagAttract magnetic beads on the automated BioCel extraction instrument.

Southern Blotting:
  DNA was extracted from lyophilized whole leaf tissue samples. Samples were ground using tungsten beads with grinding in a modified "paint shaker". Samples were extracted following a standard Cetyltrimethylammonium Bromide (CTAB) extraction method. Samples were resuspended overnight in 1 ml of 1×TE (Tris:EDTA) buffer.

DNA Quantification and Normalization:
  After gDNA extraction, DNA samples were quantified with the Pico Green reagent according to manufacturer's instructions (Molecular Probes, Eugene, Oreg., catalog # P7581). Pico Green readings were obtained by using the Molecular Devices Gemini XS Fluorescence Reader.
  For INVADER® assays, DNA samples were normalized to 12 ng/µL.
  For PCR analysis, DNA samples were diluted with molecular biology grade water (5 PRIME, catalog #2500020) to result in a concentration of 5-100 ng/µL. For Southern analysis, DNA samples were normalized to result in a concentration of 100 ng/µl (10 µg total DNA).

DNA Detection Assays:
  INVADER®:
  Validation of the zygosity analysis was performed using customized assay kits manufactured by Hologic formerly known as Third Wave Technologies, (Madison, Wis.) which utilized a FRET probe specific sequence (AAD1) to detect gene copy number by use of the manufacturer's INVADER® technology. The INVADER® chemistry is composed of two simultaneous isothermal reactions. A primary reaction specifically and accurately detects single-base changes, insertions, deletions and changes in gene and chromosome number for genetic, pharmacogenetic and infectious diseases. A second reaction is used for signal amplification and generic readout.

The Reaction mix consisted of 1.4 µL of Cleavase XI Fret Mix, 0.44 MgCL2, and 1.24 µL specific Oligo mix. 3 µl of denatured gDNA at the 12 ng/µL was added to 3 µl of reaction assay mix for a total volume of 6 µl per sample. Samples were incubated on a standard thermocycler with conditions set at 63° C. for 2 hours. Fluorescence readings with the Internal Control gene at 485 nm/535 nm and the nucleotide sequence of interest at 560 nm/612 nm were taken using the Tecan GENios plate reader and analyzed with the Xflour4 software.

qPCR Assays for Validation:
  TaqMan® analysis for validation was performed using an assay which was optimized for the use on the Roche LightCycler® 480 and Life Technologies' 7900HT & ViaA7 systems. This method utilized three separate biplex assays consisting of oligonucleotides specific to the AAD1 gene and to the corn endogenous reference gene, INV (Invertase); Event Specific 278 and to the corn endogenous reference gene, INV; or Event Specific 474 and to the corn endogenous reference gene, INV. Zygosity/copy number is determined by the relative intensity of fluorescence specific for AAD1 to the reference DNA.

The triplex assay consisted of the nucleotide sequence of interest (AAD1 gene)+one Event Specific (278 or 474)+the corn endogenous reference gene, INV. To detect AAD1, gene specific or the Event Specific 278 or 474, a DNA fragment is amplified with one primer/probe set containing a probe labeled with FAM fluorescent dye and INV with Cy5 fluorescence. Reference to Primer and Probe sequences are found in Table 1, and assay conditions are referenced in Tables 2 and 3.

TABLE 1

| Name | Description | 5' to 3' sequence |
|---|---|---|
| | Event Target Reaction | |
| Corn278-F | Forward Primer | ATTCTGGCTTTGCTGTAAATCGT (SEQ ID NO: 1) |
| Corn278-R | Reverse Primer | TTACAATCAACAGCACCGTACCTT (SEQ ID NO: 2) |
| Corn278-Pr | Probes (Multiplex combinations) | FAM-CTAACCTTCATTGTATTCC-MGB (SEQ ID NO: 3) |
| | | VIC-CTAACCTTCATTGTATTCC-MGB (SEQ ID NO: 4) |
| GAAD1F | Forward Primer | TGTTCGGTTCCCTCTACCAA (SEQ ID NO: 5) |
| GAAD1R | Reverse Primer | CAACATCCATCACCTTGACTGA (SEQ ID NO: 6) |
| GAAD1Pr | Probes (Multiplex combinations) | FAM-CACAGAACCGTCGCTTCAGCAACA-MGB (SEQ ID NO: 7) |
| | | HEX-CACAGAACCGTCGCTTCAGCAACA-BHQ2 (SEQ ID NO: 8) |
| | | Cy5-CACAGAACCGTCGCTTCAGCAACA-BHQ2 (SEQ ID NO: 9) |
| Corn474-F | Forward Primer | GATCGCCCTTCCCAACAGT (SEQ ID NO: 10) |
| Corn474-R | Reverse Primer | TGGCAGATGCTAGCGCTTAG (SEQ ID NO: 11) |
| Corn474-Pr | Probes (Multiplex combinations) | FAM-TTGTGTGCAAATCACGAC-MGB (SEQ ID NO: 12) |
| | Invertase Reference System Reaction | |
| INVF | Forward Primer | TGGCGGACGACGACTTGT (SEQ ID NO: 13) |
| INVR | Reverse Primer | AAAGTTTGGAGGCTGCCGT (SEQ ID NO: 14) |
| INV-Pr | Probes (Multiplex combinations) | HEX-CGAGCAGACCGCCGTGTACTTCTACC-BHQ2 (SEQ ID NO: 15) |
| | | FAM-CGAGCAGACCGCCGTGTACTTCTACC-BHQ1 (SEQ ID NO: 16) |
| | | CY5-CGAGCAGACCGCCGTGTACTTCTACC-BHQ2 (SEQ ID NO: 17) |

TABLE 2

Real Time PCR Set-up for ROCHE LC480

| | Reagent Mix | Amt (mL) | Stock |
|---|---|---|---|
| GOI | 2 X Buffer | 5 | 2x |
| | GOIFP | 0.4 | 10 mM |
| | GOIRP | 0.4 | 10 mM |
| | GOI Probe | 0.4 | 5 mM |
| IR | IC FP | 0.4 | 10 mM |
| | IC RP | 0.4 | 10 mM |
| | IC Probe | 0.4 | 5 mM |
| | H2O | 0.6 | |
| | DNA | 2 | |
| | Total | 10 | |

TABLE 3

Real Time PCR Set-up for ROCHE LC480 Corn Triplex

| | Roche Mix | Amt (mL) | Stock |
|---|---|---|---|
| GOI | 2 X Buffer | 5 | 2x |
| | GOIFP | 0.2 | 20 mM |
| | GOIRP | 0.2 | 20 mM |
| | GOI Probe | 0.2 | 10 mM |
| | GOIFP | 0.2 | 20 mM |
| | GOIRP | 0.2 | 20 mM |
| | GOI Probe | 0.2 | 10 mM |
| IR | IC FP | 0.2 | 20 mM |
| | IC RP | 0.2 | 20 mM |
| | IC Probe | 0.2 | 10 mM |
| | H2O | 1.2 | |
| | DNA | 2 | |
| | Total | 10 | |

The multiplex PCR conditions for amplification were:

1× Roche PCR Buffer, 0.4 µM event specific forward primer, 0.4 µM event specific reverse primer, 0.4 µM Primer INVF, 0.4 µM Primer INVR, 0.2 µM Event specific probe, 0.2 µM INV Probe, 0.1% PVP, and 20 ng gDNA in a total reaction of 10 µl.

The assay mixture was amplified using the following conditions: i) 95° C. for 10 min., ii) 95° C. for 10 sec., iii) 59° C. for 35 sec., iv) 72° C. for 1 sec., and v) repeat step ii-iv for 40 cycles, v) 40° C. hold.

The Real time PCR was carried out on the Roche LightCycler 480. Data analysis was based on measurement of the crossing point (Cp value) determined by LightCycler 480 software, which is the PCR cycle number when the rate of change in fluorescence reaches its maximum.

qPCR for High-Throughput Zygosity (HTMA Assays):

TaqMan® analysis by endpoint and qPCR were performed on plant breeding samples to compare Zygosity/copy number results for the detection of a possible unintended event contamination.

End-Point TaqMan Assays:

The End-Point TaqMan assay consisted of Event Specific plus Wild-type specific primers and probes dependent upon crop and Event.

For an Event Specific amplification: An event-specific oligonucleotide probe binds to the amplicon between a single event specific primer and a common reverse primer located on the 3' flanking genomic DNA. The probe is labeled with FAM as a fluorescent reporter dye at the 5' end and MGBNFQ (minor grove binding non-fluorescent quencher) as a quencher at the 3' end.

For the wild-type amplification: Wild-type specific forward primer is located on 5' flanking genomic DNA, and utilizes the same common reverse primer as found in the event specific reaction. These primers positioned on either side of the transgene insertion, amplify a fragment only in the absence of the transgene. A probe labeled with VIC and MGBNFQ is designed to the 3' flanking genomic sequence and is detected in the presence of the wild-type amplicon. The EndPoint PCR working conditions for amplification were:

2XGTXpress, (TaqMan® Gene Expression master mix, Applied Biosystems), 8× Assay Mix (pre-made mixture consisting of specific primer and probes), 1% PVP, and 1 µl of gDNA in a total reaction of 3 µl.

The assay mixture was amplified using the following conditions on a GenAmp PCR System 9700: i) 95° C. for 10 min., ii) 95° C. for 15 sec., iii) 60° C. for 60 sec., and iv) repeat step ii-iii for 40 cycles.

Following completion of the TaqMan® PCR, fluorescence reading on a spectrofluorometer (BioTek Synergy H4 or Tecan GENios) was performed with a table and distribution graph generated in Microsoft Office Excel. The 'null', 'hemizygous', and 'homozygous' controls of similar genotypic background served as negative and positive controls.

qPCR (Real-Time PCR) Assays:

The qPCR Real-time TaqMan assay consisted of specific primers and probes for a Gene Specific (nucleotide sequence of interest) plus a endogenous internal control gene, which was dependent upon crop and nucleotide sequence of interest. To determine Zygosity/copy number of the nucleotide sequence of interest, a DNA fragment is amplified with one TaqMan® primer/probe set containing a probe labeled with FAM fluorescent dye for the nucleotide sequence of interest plus a primer set containing a VIC labeled probe specific to the crop endogenous reference sequence which are amplified in the same reaction well.

The qPCR working conditions for amplification were:

XGTXpress, (TaqMan® Gene Expression master mix, Applied Biosystems), 8× Assay Mix (pre-made mixture consisting of specific primer and probes), 1% PVP, 1 µl of gDNA in a total reaction of 3 µl.

The assay mixture was amplified using the following conditions on an ABI 7900HT Fast Real-Time PCR System, Applied Biosystems): i) 95° C. for 10 min., ii) 95° C. for 15 sec., iii) 60° C. for 60 sec., and iv) repeat step ii-iii for 40 cycles.

Following completion of the Real-time TaqMan® PCR, data was analyzed using the SDS software on the ABI 7900HT following a standard ΔΔCt (RQ) method for Zygosity calls.

Southern Blots:
Restriction Digests:

The restriction digestions using the enzymes AflII+SwaI and NcoI were set up per the manufacturer's (NEB, New England Biolabs) protocol. The samples were incubated overnight at 37° C. and DNA precipitations were carried out using Isopropanol with NaCl concentration adjusted to 0.1M.

Gel Electrophoresis:

Samples were loaded using 3× loading dye onto a 0.8% agarose gel prepared in 0.4×TAE buffer. Gel electrophoresis was carried out overnight at a constant 55 volts.

Transfer and Hybridization:

A traditional capillary transfer apparatus was used and the gel was transferred overnight. A Hybond positive charged membrane was used and the DNA fixed to the membrane by baking at 65° C. for at least one hour. Pre-hybridization in Perfect Hyb Plus Buffer, Sigma cat#H7033 was carried out for at least 2 hours at 65° C. in a hybridization oven. Hybridization was carried out overnight using a P[32] radioactive probe specific for the gene of interest (GOI) AAD1. Post-hybridization washes were done at 65° C. in a shaker[6].

Exposure:

The Southern membrane was exposed to imaging screens for 24 hours to 72 hours and detected using a Phosphor imager.

Example 2: Initial Validation

Figure 2:
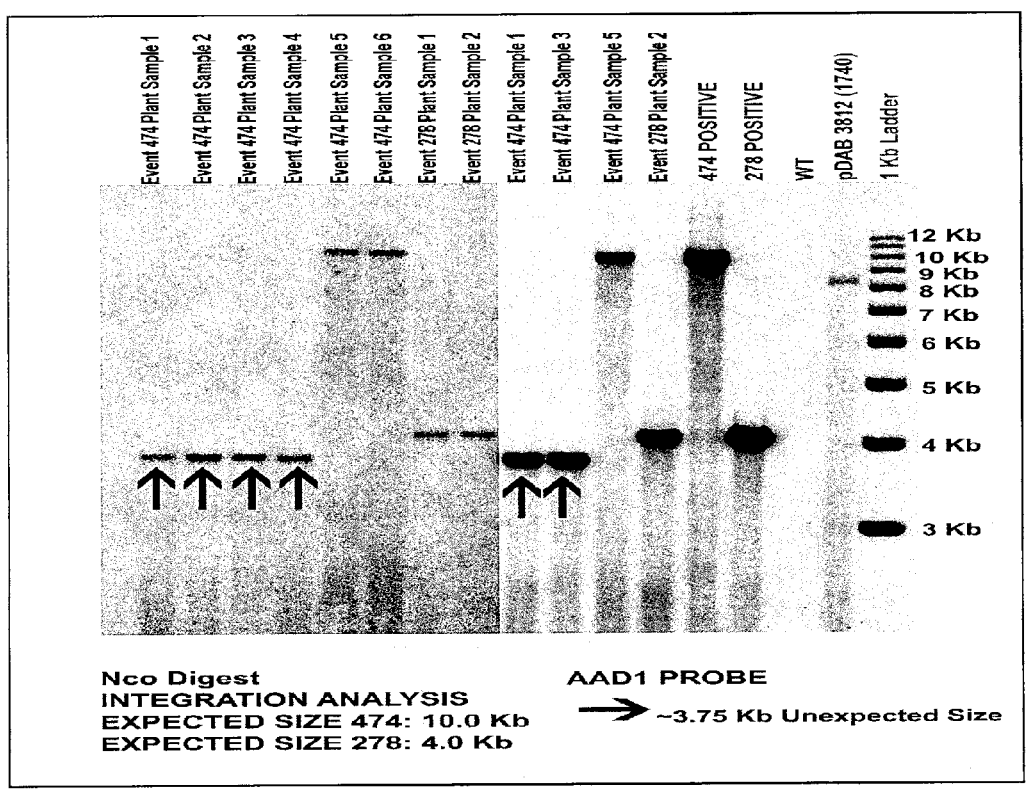
FIG. 2 is a depiction of Southern blot data that detected an unexpected size band in four AAD1 Event 474 plant samples within two different plant lineages as indicated by the arrows in Samples 1-4. The expected Southern band size with the NcoI restriction digest with the AAD1 probe was 10 Kb as indicated by the 474 positive control sample. This Southern data also shows plant samples 5 and 6 were the expected event with a 10 Kb band size. This data indicated a population of mixed AAD1 events.

The initial validation of combining two TaqMan assays for the detection of an unintended event was compared to the tradition method of Southern blot analysis. A smaller sample set (approximately 100 samples) of the same field population were analyzed by Southern blot which demonstrated an unexpected band size in two different plant lineages (Refer to FIG. 2). This Southern data concluded that this field plant population had an adventitious AAD1 event contamination.

Several plant samples from field populations were also analyzed for a nucleotide sequence of interest (AAD1) using INVADER® and/or TaqMan technology and an Event Specific assay for events 278 and 474 using TaqMan technology. The zygosity/copy number data generated from this analysis were compared between the Event Specific and the Gene Specific assays for each plant sample.

Figure 3:
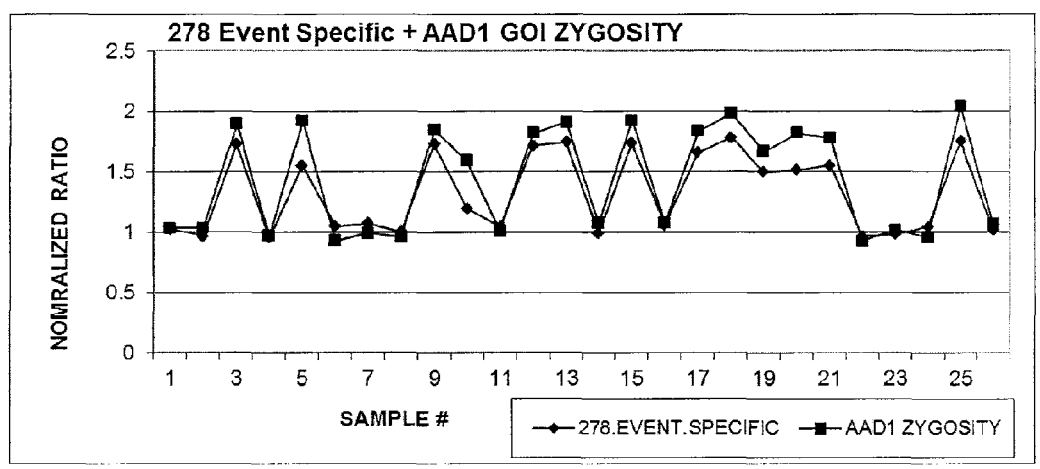
FIG. 3 is a graphical depiction of a data set showing that the Zygosity Copy number calls of the GOI (AAD1) and the Event Specific 278 are the same. This indicates these plant samples contain the expected event with no contaminating event present.

When the nucleotide sequence of interest and Event Specific data points "matched", it was determined that the correct Event was present with the correct nucleotide sequence of interest copy number (refer to FIG. 3). The data demonstrates both Hemizygous (normalized ratio ~1) and Homozygous (normalized ratio>1.5) plants with each plant having matching Zygosity calls for both the nucleotide sequence of interest (AAD1) and Event 278 assays. The data set for Event 278 plant population, confirmed the Southern blot data which also did not detect an unknown AAD1 event contamination in this field population.

Figure 4:
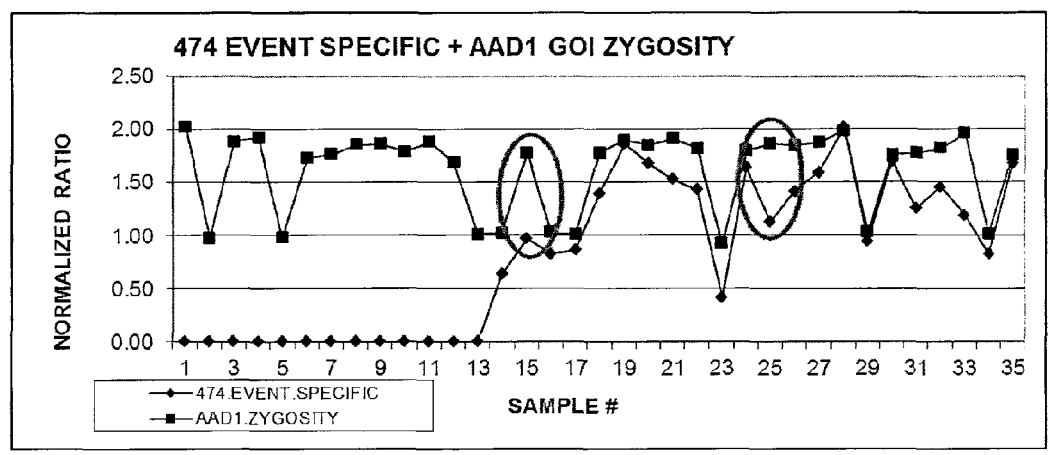
FIG. 4 is a graphical depiction of a data set showing that sample numbers 1 to 13 have one or two copies for the GOI AAD1 but zero copies for the 474 Event, indicating an unknown different AAD1 Event was detected. The red circles in Chart 2 show two copies of the GOI but only one copy of the Event Specific Assay indicating plants with possible "mixed" AAD1 events.

However, when analysis of the nucleotide sequence of interest copy number found instances where the nucleotide sequence of interest was "Higher" than the corresponding Event Specific copy number (the data points did not "Match" each other), it was determined that an unintended Event was detected and thus present in the Event 474 plant population (refer to FIG. 4). The data set for the Event 474 plant population indicated the presence of an unknown AAD1 event. This data is correlated to the Southern blot analysis of this same plant population.

Example 3: Single Tube Assay

Figure 5:
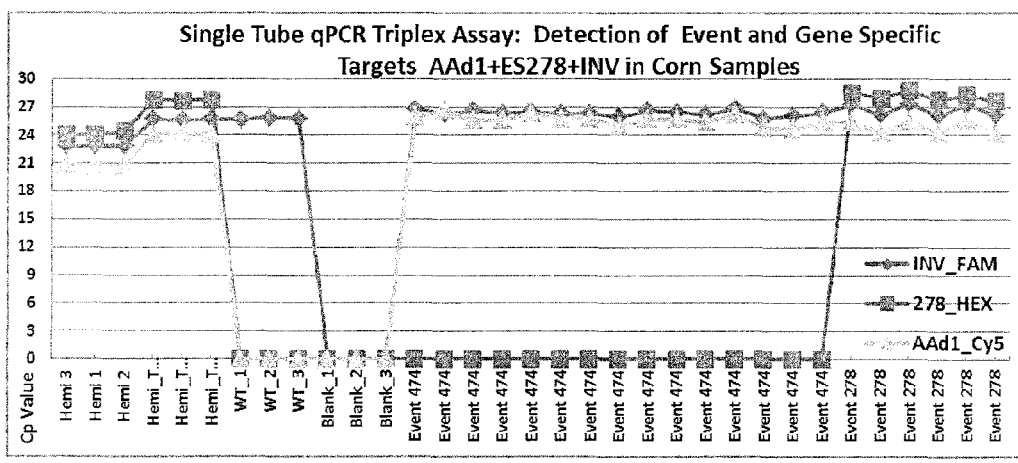
FIG. 5 is a graphical depiction of a data set showing that within a single tube, the assay detected the AAD1 (GOI)+ Event Specific 278 in the correct samples. The known Event 278 samples were positive for both AAD1 (GOI) and Event Specific 278 along with the Internal Control gene. In the 474 samples, only the AAD1 (GOI) and Internal control were detected with no detection of 278 Event Specific. Also, all the known controls showed the expected results: Hemizygous with amplification of AAD1/ES278/Invertase, Wild-type with only Internal Control Invertase (INV), and Blanks with no amplification.
Figure 6A:
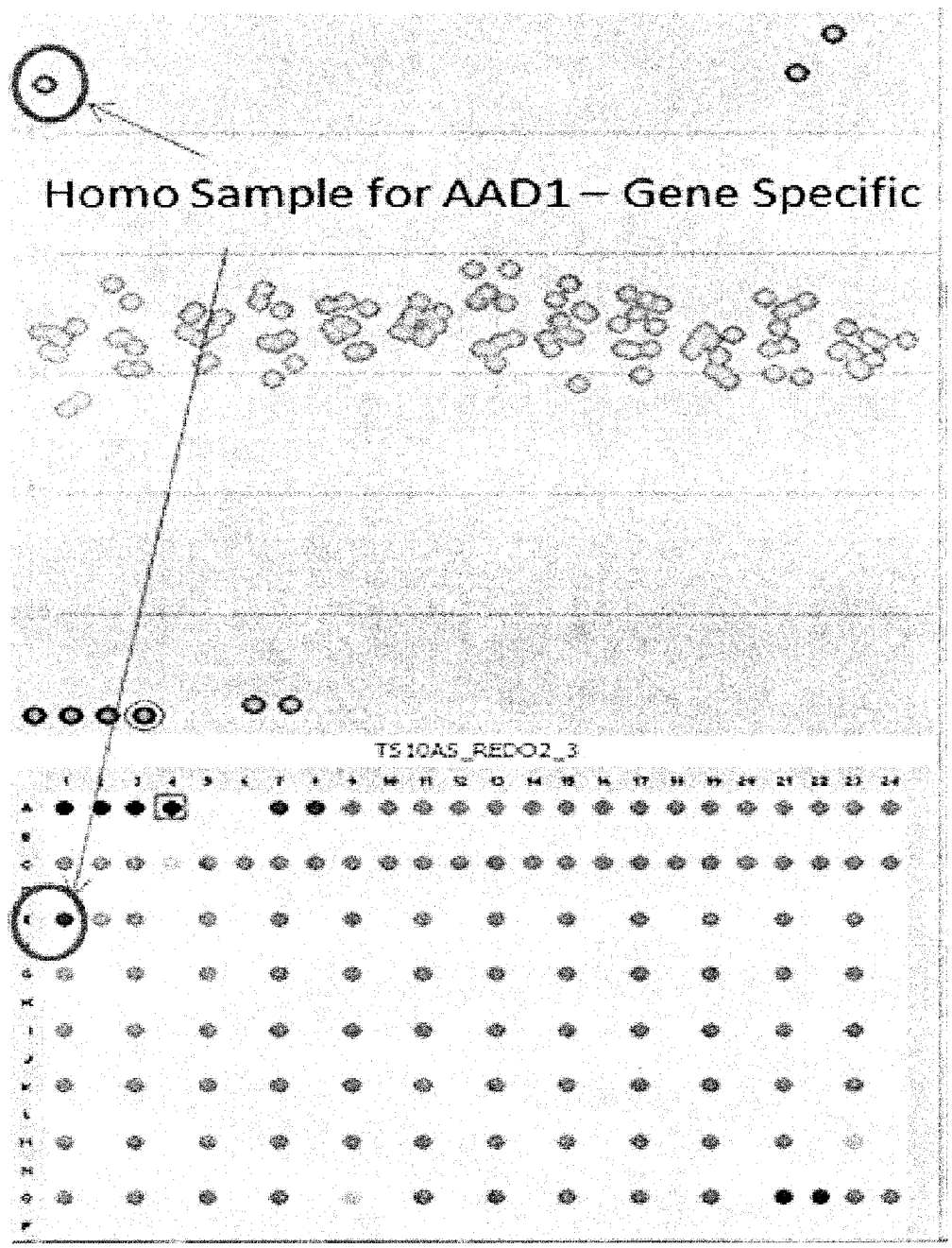
FIG. 6A is a graphical depiction of a data set showing the ability for this methodology to detect the unintended presence of an event with the same GOI (AAD1) using the Gene Specific assay.
Figure 6B:
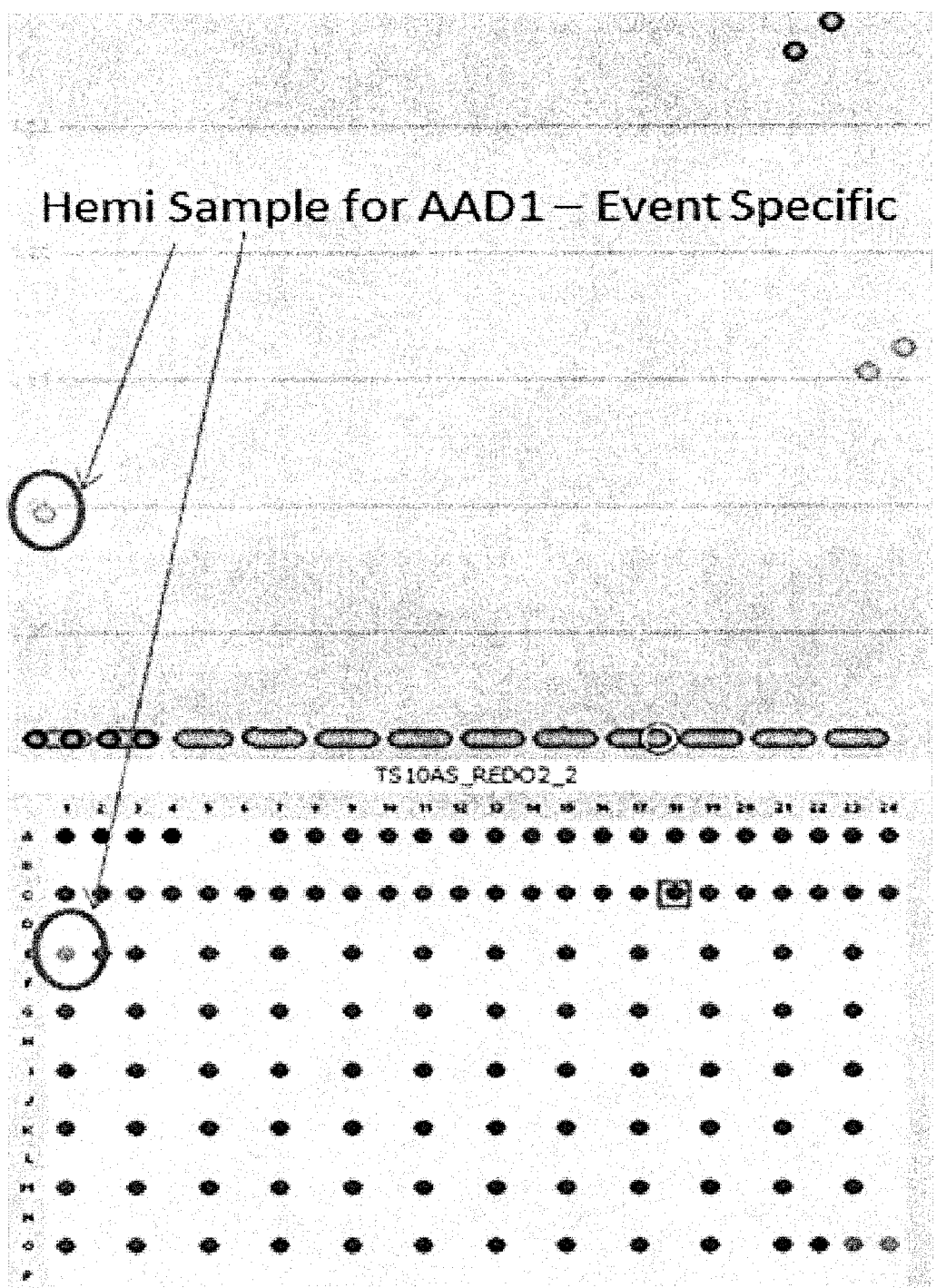
FIG. 6B is a graphical depiction of a data set showing the ability for this methodology to detect the unintended presence of an event with the same GOI (AAD1) using the Event Specific assay. The dot in the circle of FIG. 6A indicates a sample with an elevated copy number for the GOI AAD1 but the same sample is Hemizygous for the 278 Event Specific shown as the dot in the circle on FIG. 6B. This demonstrates discordance between the copy number and zygosity state for this plant indicating a contaminating event.

To further optimize the throughput of this new combination of assays, a single tube real-time qPCR assay was developed and tested against a plant population with the same GOI (AAD1) but mixed Events (278 and 474). This triplex assay allowed the detection of the GOI, Event Specific and the internal reference gene in one reaction well for the same plant sample. A combination of three fluorescent dyes consisting of FAM, HEX and Cy5 were used for the internal control gene, Event specific 278 and AAD1 GOI, respectively. This assay demonstrated that Event 278 was detected in known AAD1/278 plant samples but was not detected in known AAD1/Event 474 plant samples (Refer to FIG. 5 for data analysis).

This assay could also provide copy number analysis but was not completed on these test samples.

The methodology of using the analysis of an Event specific assay plus a GOI (gene of interest) assay to detect a possible unintended event was applied in high-throughput Zygosity analysis for the corn and soybean breeding programs within Dow AgroSciences. In the last two years, approximately 50,000 corn samples and 32,000 soybean samples have been analyzed using this methodology.

The data generated used TaqMan primer and probes on an ABI 7900 Fast real-time PCR System to establish Zygosity calls on the plant samples. This technology was applied primarily on confirmation calls and/or back-cross generation samples and was able to detect an unintended event.

In the soybean breeding program, AAD12 and PAT GOI assays were run alongside the Dow AgroSciences developed Event 416 Specific assay to detect an unintended soybean event within the population (data not displayed). Sample data for the AAD1 and Event 278 in the corn breeding samples is displayed in chart 6A and 6B where contamination in this sample population was detected.

What is claimed is:

1. A method of determining if a contaminating integration of a nucleotide sequence of interest is present in a nucleic acid sample from an organism, the method comprising:
performing a first assay to provide a first value indicative of the total number of iterations of the nucleotide sequence of interest in the nucleic acid sample;
performing a second assay to provide a second value indicative of the number of iterations of the nucleotide sequence of interest at a particular integration site in the nucleic acid sample;
comparing the first value to the second value, wherein the first value being greater than the second value indicates the presence of a contaminating integration;
performing a third assay to provide a third value indicative of the total number of iterations of a control nucleotide sequence in the nucleic acid sample,
wherein the zygosity/copy number of the control nucleotide sequence in the nucleic acid sample is known, and
determining the zygosity/copy number of the nucleotide sequence of interest by comparing the first value with the third value,
wherein the first assay, the second assay, and the third assay are performed in the same volume at the same time.

2. The method according to claim 1, wherein the organism is a plant.

3. The method according to claim 2, wherein the plant is corn, soybean, rapeseed, cotton, or wheat.

4. The method according to claim 1, wherein the first assay is selected from the group consisting of PCR, Invader, Scorpion, KASPAR, and hybridization type assays.

5. The method according to claim 1, wherein the second assay is selected from the group consisting of PCR, Invader, Scorpion, KASPAR, and hybridization type assays.

6. The method according to claim 1, wherein the first assay comprises performing a PCR with a set of primers, wherein the primers are complementary to binding sites internal to the nucleotide sequence.

7. The method according to claim 1, wherein the second assay comprises performing a PCR with a set of primers, one primer being complementary to a binding site outside the nucleotide sequence of interest and one primer being complementary to a binding site internal to the nucleotide sequence of interest.

8. The method according to claim 1, wherein the third assay comprises:
    performing a PCR with a set of primers, wherein the primers are complementary to sites in the set of nucleic acids; and
    determining the third value as a value for the amount of the PCR product resulting from the PCR of the set of primers,
    wherein a portion of the nucleotide sequence of interest is not present in the PCR product of the third set of primers; and
    wherein the zygosity/copy number of the sites to which the set of primers is complementary is known.

9. A method of determining if a contaminating integration of a nucleotide sequence of interest is present in a nucleic acid sample from an organism, the method comprising:
    generating a first amplicon from the nucleic acid sample with a first set of primers that are complementary to binding sites internal to the nucleotide sequence of interest, and determining a first value from the amount of the first amplicon;
    generating a second amplicon from the nucleic acid sample with a second set of primers, one primer of the second set being complementary to a binding site outside the nucleotide sequence of interest, and one primer of the second set being complementary to a binding site internal to the nucleotide sequence of interest and determining a second value from the amount of the second amplicon;
    generating a third amplicon from the nucleic acid sample comprising a control nucleotide sequence that is present in the nucleic acid sample in a known number of iterations, and determining a third value from the amount of the third amplicon;
    determining the presence or absence of a contaminating integration by comparing the first value to the second value, wherein the first value being greater than the second value indicates the presence of a contaminating integration; and
    determining the zygosity/copy number of the nucleotide sequence of interest by comparing the first value with the third value,
    wherein the first assay, the second assay, and the third assay are performed in the same volume at the same time.

10. The method according to claim 9, wherein the first and second amplicons are generated in the presence of probes which provide a detectable signal when the first amplicon and the second amplicon are produced.

11. The method according to claim 10, wherein a first probe binds to a site in the first amplicon.

12. The method according to claim 11, wherein a second probe binds to a site in the second amplicon that bridges the particular integration site of the nucleotide sequence of interest.

13. The method according to claim 10, wherein the probes are TaqMan probes.

14. The method according to claim 9 wherein the first, second, and third amplicons are generated in the presence of probes which provide a detectable signal hybridized to an amplicon.

15. The method according to claim 14, wherein the probes are TaqMan probes.

* * * * *

SEQUENCE LISTING

```
<160> NUMBER OF SEQ ID NOS: 17

<210> SEQ ID NO 1
<211> LENGTH: 23
<212> TYPE: DNA
<213> ORGANISM: Artificial Sequence
<220> FEATURE:
<223> OTHER INFORMATION: Corn 278-F forward primer

<400> SEQUENCE: 1
attctggctt tgctgtaaat cgt                                              23

<210> SEQ ID NO 2
<211> LENGTH: 24
<212> TYPE: DNA
<213> ORGANISM: Artificial Sequence
<220> FEATURE:
<223> OTHER INFORMATION: Corn278-R reverse primer

<400> SEQUENCE: 2
ttacaatcaa cagcaccgta cctt                                             24

<210> SEQ ID NO 3
<211> LENGTH: 19
<212> TYPE: DNA
<213> ORGANISM: Artificial Sequence
<220> FEATURE:
<223> OTHER INFORMATION: Corn278-PR probe

<400> SEQUENCE: 3
ctaaccttca ttgtattcc                                                   19

<210> SEQ ID NO 4
<211> LENGTH: 19
<212> TYPE: DNA
<213> ORGANISM: Artificial Sequence
<220> FEATURE:
<223> OTHER INFORMATION: Corn278-Pr probe

<400> SEQUENCE: 4
ctaaccttca ttgtattcc                                                   19

<210> SEQ ID NO 5
<211> LENGTH: 20
<212> TYPE: DNA
<213> ORGANISM: Artificial Sequence
<220> FEATURE:
<223> OTHER INFORMATION: GAAD1F forward primer

<400> SEQUENCE: 5
tgttcggttc cctctaccaa                                                  20

<210> SEQ ID NO 6
<211> LENGTH: 22
<212> TYPE: DNA
<213> ORGANISM: Artificial Sequence
<220> FEATURE:
<223> OTHER INFORMATION: GAAD1R reverse primer
```

```
<400> SEQUENCE: 6
caacatccat caccttgact ga                                          22

<210> SEQ ID NO 7
<211> LENGTH: 24
<212> TYPE: DNA
<213> ORGANISM: Artificial Sequence
<220> FEATURE:
<223> OTHER INFORMATION: GAAD1Pr probe

<400> SEQUENCE: 7
cacagaaccg tcgcttcagc aaca                                        24

<210> SEQ ID NO 8
<211> LENGTH: 24
<212> TYPE: DNA
<213> ORGANISM: Artificial Sequence
<220> FEATURE:
<223> OTHER INFORMATION: GAAD1Pr probe

<400> SEQUENCE: 8
cacagaaccg tcgcttcagc aaca                                        24

<210> SEQ ID NO 9
<211> LENGTH: 24
<212> TYPE: DNA
<213> ORGANISM: Artificial Sequence
<220> FEATURE:
<223> OTHER INFORMATION: GAAD1Pr probe

<400> SEQUENCE: 9
cacagaaccg tcgcttcagc aaca                                        24

<210> SEQ ID NO 10
<211> LENGTH: 19
<212> TYPE: DNA
<213> ORGANISM: Artificial Sequence
<220> FEATURE:
<223> OTHER INFORMATION: Corn474-F forward primer

<400> SEQUENCE: 10
gatcgccctt cccaacagt                                              19

<210> SEQ ID NO 11
<211> LENGTH: 20
<212> TYPE: DNA
<213> ORGANISM: Artificial Sequence
<220> FEATURE:
<223> OTHER INFORMATION: Corn474-R reverse primer

<400> SEQUENCE: 11
tggcagatgc tagcgcttag                                             20

<210> SEQ ID NO 12
<211> LENGTH: 18
<212> TYPE: DNA
<213> ORGANISM: Artificial Sequence
<220> FEATURE:
<223> OTHER INFORMATION: Corn474-Pr probe

<400> SEQUENCE: 12
ttgtgtgcaa atcacgac                                               18

<210> SEQ ID NO 13
```

-continued

```
<211> LENGTH: 18
<212> TYPE: DNA
<213> ORGANISM: Artificial Sequence
<220> FEATURE:
<223> OTHER INFORMATION: Invertase forward primer

<400> SEQUENCE: 13
tggcggacga cgacttgt                                                       18

<210> SEQ ID NO 14
<211> LENGTH: 19
<212> TYPE: DNA
<213> ORGANISM: Artificial Sequence
<220> FEATURE:
<223> OTHER INFORMATION: Invertase reverse primer

<400> SEQUENCE: 14
aaagtttgga ggctgccgt                                                      19

<210> SEQ ID NO 15
<211> LENGTH: 26
<212> TYPE: DNA
<213> ORGANISM: Artificial Sequence
<220> FEATURE:
<223> OTHER INFORMATION: Invertase probe

<400> SEQUENCE: 15
cgagcagacc gccgtgtact tctacc                                              26

<210> SEQ ID NO 16
<211> LENGTH: 26
<212> TYPE: DNA
<213> ORGANISM: Artificial Sequence
<220> FEATURE:
<223> OTHER INFORMATION: Invertase probe

<400> SEQUENCE: 16
cgagcagacc gccgtgtact tctacc                                              26

<210> SEQ ID NO 17
<211> LENGTH: 26
<212> TYPE: DNA
<213> ORGANISM: Artificial Sequence
<220> FEATURE:
<223> OTHER INFORMATION: Invertase probe

<400> SEQUENCE: 17
cgagcagacc gccgtgtact tctacc                                              26
```